United States Patent [19]

Fiege et al.

[11] 4,221,719

[45] Sep. 9, 1980

[54] PROCESS FOR THE PREPARATION OF ARYLGLYOXYLIC ACIDS

[75] Inventors: Helmut Fiege, Leverkusen; Karlfried Wedemeyer, Cologne, both of Fed. Rep. of Germany

[73] Assignee: Bayer Aktiengesellschaft, Leverkusen, Fed. Rep. of Germany

[21] Appl. No.: 62,846

[22] Filed: Aug. 1, 1979

[30] Foreign Application Priority Data

Aug. 19, 1978 [DE] Fed. Rep. of Germany ...... 2836327

[51] Int. Cl.² ............... C07D 317/06; C07C 51/42
[52] U.S. Cl. ............................ 260/340.5 R; 562/421
[58] Field of Search ............... 260/340.5; 562/421

[56] References Cited

U.S. PATENT DOCUMENTS 3,711,523  1/1973  Pultinas ........................ 562/421

Primary Examiner—Alan Siegel

Attorney, Agent, or Firm—Sprung, Felfe, Horn, Lynch & Kramer

[57] ABSTRACT

Process for the preparation of an arylglyoxylic acid of the formula Ar—CO—COOH, wherein Ar is optionally substituted aryl, which process comprises oxidizing the corresponding arylethane-1,2-diol of the formula

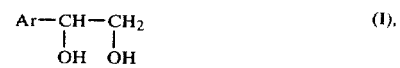

with oxygen or a gas containing molecular oxygen, in an aqueous alkaline medium and in the presence of a platinum-group metal catalyst and, as an activator, a material selected from lead, lead compounds, bismuth and bismuth compounds, at a temperature of up to the boiling point of the reaction mixture; e.g. phenylglyoxylic acid is produced from phenylethane-1,2-glycol preferably using platinum activated with lead, bismuth, or compounds thereof.

30 Claims, No Drawings

PROCESS FOR THE PREPARATION OF ARYLGLYOXYLIC ACIDS

The present invention relates to a process for the preparation of arylglyoxlylic acids; more specifically the invention provides such a process involving the oxidation of arylethane-1,2-diol compounds.

Arylglyoxylic acids are valuable intermediates in organic synthesis, for example for the preparation of plant protection agents.

The oxidation of phenylethane-1,2-diol to phenylglyoxylic acid can formally take place via the following intermediate stages (see Rodd's Chemistry of Carbon Compounds, volumn III, part E, 2nd edition (1974), page 71 et seq.):

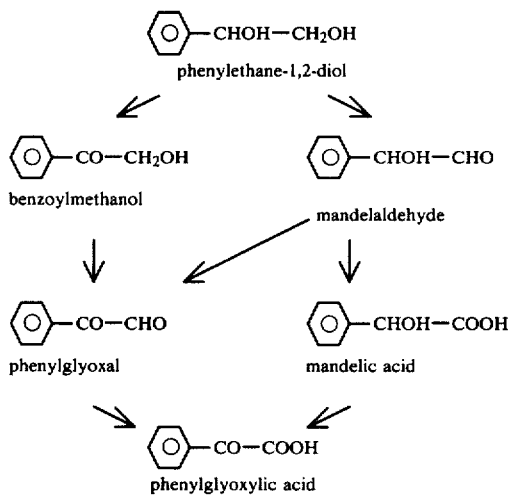

Each of these compounds is structurally predestined to undergo numerous side-reactions, especially oxidative scissions (to one or more of benzaldehyde, benzoic acid, formaldehyde, formic acid and $CO_2$). The chance of selectively arriving at phenylglyoxylic acid in one step by oxidation of phenylethane-1,2-diol is thus extremely low. This is confirmed by the results known from the literature: although mandelic acid can—if only in poor yield—by oxidised to phenylglyoxylic acid (see Organic Synthesis, Coll. vol I, 2nd edition, 1956, pages 241 to 245), the oxidation of phenylethane-1,2-diol with potassium permanganate leads virtually completely to benzoic acid (see J. Am. Chem. Soc. 35 (1913), pages 54–68). Essentially oxidative scission also takes place on oxidation of phenylethane-1,2-diol with chromic acid, potassium ferricyanide, silver oxide or bromine (see the preceding literature reference), or on oxidation with nickel peroxide (see Chem. Pharm. Bull. (Tokyo) 12 (1964), 403–7), with potassium periodate (see Talanta 23 (1976), pages 237–9) or with lead tetraacetate (see Rodd's Chemistry of Carbon Compounds, volume III, part E, 2nd edition (1974), page 74). Using nitric acid, the oxidation stops, under mild conditions, at the stage of benzoylmethanol; under more severe, industrially rather unattractive, conditions, benzoylformic acid has been detected qualitatively alongside benzoic acid, (Liebigs Annalen der Chemie 216 (1883), page 313; Ber. Dtsch. Chem. Ges. 10 (1877), page 1,488). Using electrochemical oxidation of phenylethane-1,2-diol, even under the most advantageous conditions (platinised platinum anodes), phenylglyoxylic acid was only obtainable in minor amounts (alongside mandelic acid, benzoic acid, formic acid and $CO_2$) (see Ann. Acad. Sci. fenn. [A] 39 No. 11 (1934), page 63).

Accordingly, no process is known which permits selective oxidation of phenylethylene-1,2-glycol to phenylglyoxylic acid under industrially interesting conditions.

The present invention now provides a process for the preparation of an arylglyoxylic acid, in which an arylethane-1,2-diol of the general formula

in which

Ar represents optionally substituted aryl, is oxidised with oxygen or a gas that contains molecular oxygen in an aqueous alkaline medium in the presence of a catalyst comprising a platinum-group metal (as hereinafter defined) and in the simultaneous presence, as an activator, of lead and/or a compound thereof and/or bismuth and/or a compound thereof, at a temperature up to the boiling point of the reaction mixture.

The arylethane-1,2-diols (I) can be present in the R—, S— or (±)-form. Mixtures of different arylethane-1,2-diols can also be employed for the oxidation.

In view of the prior art, it must be described as distinctly surprising that the otherwise usual oxidative scission substantially does not occur under the conditions of the process according to the invention and that it proves possible, in a technically simple manner, to convert arylethane-1,2-diols, for example phenylethane-1,2-diol (phenylethylene-1,2-glycol), into arylglyoxylic acids, for example phenylglyoxylic acid, with very high yield and purity, that is to say highly selectively.

In addition, the process according to the invention exhibits a number of other advantages. Thus, the oxidising agent used is oxygen, which is generally available, is cheap and does not lead to secondary products of the oxidising agent which pollute the environment. As a result of the high selectivity, fewer by-products, which have to be separated off and removed, are formed; this means, at the same time, that the wastage of valuable raw materials is avoided. Further technical advantages are that the reaction conditions permit good removal of heat, the pH value of the reaction medium allows the reaction to be carried out even in steel apparatus, and the oxidation can be effectively controlled via the oxygen uptake.

If phenylethylene-1,2-glycol is used as the starting compound, the overall course of the reaction can be represented by the following equation:

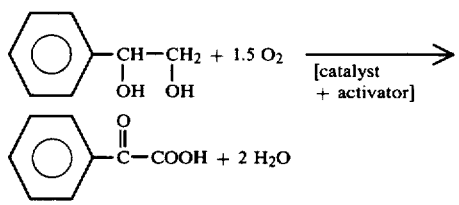

The formula (I) provides a general definition of the arylethane-1,2-diols to be used as starting materials according to the invention. In this formula, Ar preferably represents phenyl. The radical Ar further represents substituted aryl, the substituents preferably being selected independently from: alkyl (preferably with 1 to 6 C atoms), cycloalkyl (preferably with 3 to 6 C atoms), aryl (preferably phenyl), aralkyl (preferably benzyl), alkoxy (preferably with 1 to 6 C atoms), cycloalkoxy (preferably with 3 to 6 C atoms), aryloxy (preferably phenoxy), hydroxyl, carboxyl, halogen (especially fluorine, chlorine and bromine), and the methylenedioxy group. If the aryl radical denotes phenyl, the substituents are preferably in the 3- and/or 4- and/or 5-positions.

The arylethane-1,2-diols of the formula (I) required as starting compounds are in themselves known or can be prepared in accordance with known processes. Thus, phenylethylene-1,2-glycol can, for example, be prepared by hydroxylation of styrene with hydrogen peroxide (see Helv. chim. Acta 50 (1967), pages 319–321) or by hydrolysis of styrene oxide (for further processes, see Rodd's Chemistry of Carbon Compounds, volume III, part E, 2nd edition (1974), page 72 et seq.).

By "aqueous alkaline medium" there is to be understood a reaction mixture that reacts alkaline, that is to say has a pH value $> 7$. Advantageously, the amount of alkali is so chosen as to provide 0.3 to 5, preferably 0.5 to 3, equivalents of alkali per mole of arylethane-1,2-diol to be oxidised. The use of from 0.9 to 2 equivalents of alkali per mole of arylethane-1,2-diol to be oxidised is particularly preferred.

The alkali can be added to a solution or suspension of the arylethane-1,2-diol in water, or the arylethane-1,2-diol can be dissolved or suspended in the alkali solution.

Preferably, sodium or potassium hydroxide or carbonate is used as the alkali.

The concentration of the organic compounds in the aqueous alkaline reaction solution is in general selected so that both the arylethane-1,2-diol and the arylglyoxylic acid formed are present in solution under the reaction conditions. Where appropriate, the arylethane-1,2-diol should be added in portions to the oxidation mixture, possibly together with part of the alkali. Final concentrations of organic compounds in the reaction mixture of from 5 to 30% by weight have proved suitable.

Under the conditions according to the invention, an oxidation effect is observable at all temperatures at which a liquid phase is present. Accordingly, the possible reaction temperature ranges from the solidification point to the boiling point of the reaction mixture. Preferably, the reaction is carried out in the temperature range of 10° to 100° C.

By "platinum-group metals", which are employed as catalysts in the process according to the invention, there are to be understood the chemically closely related metals platinum, palladium, iridium, rhodium, ruthenium and osmium, which in nature generally occur together. The use of platinum or palladium, especially platinum, is preferred.

The platinum-group metal used as the catalyst can be added to the reactants in any of a great variety of forms, for example in the elementary, that is to say metallic, form, for instance as so-called "black", in combination with other platinum-group metals or in the form of a compound, for example as an oxide or also in the form of some other compound.

The platinum-group metals can be applied to supports. Examples of suitable supports are active charcoal, graphite, kieselguhr, silica gel, spinels, aluminium oxide, asbestos, calcium carbonate, magnesium carbonate, barium sulphate or also organic support materials. Active charcoals have proved particularly suitable, for example, inexpensive pulverulent active charcoals, produced from wood, which are extensively used for decolorising purposes.

The platinum-group metal content of these supported catalysts can vary within wide limits. Supported catalysts with a platinum-group metal content of less than 10% by weight, especially those with contents of 0.1 to 5% by weight of platinum-group metal, have proved particuarly suitable.

The amounts in which the platinum-group metal catalysts are used can vary within wide limits. They depend on the desired rate of oxidation, the form of the catalyst, the nature and amount of the activator, and so on, and can in a specific case easily be determined by preliminary experiments.

In general, the amount of platinum-group metal required per mole of arylethane-1,2-diol is less than 1,000 mg, and in most cases sufficiently high reaction rates are achieved with an amount of platinum-group metal of 20 to 400 mg per mole of arylethane-1,2-diol.

Since tar formation is almost completely avoided when using the above-specified activators, the catalysts can be used repeatedly. As a result of this reuse, the consumption of platinum-group metal catalyst per mole of arylethane-1,2-diol can be reduced to 5 mg or less, before reprocessing of the platinum-group metal catalyst becomes necessary.

Above all, lead and bismuth have proved suitable activators. The amounts in which the activators to be used according to the invention are employed can vary within wide limits. The activator effect manifests itself clearly even with added amounts of as little as $1 \times 10^{-5}$ mole of metal or metal compound per mole of arylethane-1,2-diol. It is also possible to employ 0.1 mole or more of activator per mole of arylethane-1,2-diol, but these large added amounts in general offer no advantage. In general, the addition of $5 \times 10^{-5}$ to $1 \times 10^{-1}$ mole, preferably $1 \times 10^{-4}$ to $1 \times 10^{-2}$ mole, of metal per mole of arylethane-1,2-diol to be oxidised has proved suitable.

The metals (Pb and Bi) to be used as activators according to the invention can be employed as such, that is to say in the elementary form, and/or in the form of their compounds, for example as oxides; or as salts of hydracids, such as chlorides, bromides, iodides, sulphides, selenides and tellurides; or as salts of inorganic oxy-acids, such as nitrates, nitrites, phosphites, phosphates, sulfates, carbonates, perchlorates, antimonates, arsenates, selenites, selenates, and borates; or as salts of oxy-acids derived from transition metals, for example vanadates, niobates, tantalates, chromates, molybdates, tungstates, and permanganates; or as salts of organic aliphatic or aromatic acids, for example formates, acetates, propionates, benzoates, salicylates, lactates, mandelates, glyoxylates, arylglyoxylates and citrates; or as phenolates and the like. The activators may, in each particular case, be soluble, partially soluble or insoluble in the reaction mixture.

Combinations of these activators with one another and/or with other elements or compounds, not specified as an activator, can also be used. The activators according to the invention may be present in various valency levels or in a mixture of valency levels; furthermore, changes in valency may also occur during the reaction. If the activators have not already been added as oxides and/or hydroxides, it is possible that they become entirely or partially converted to these in the alkaline medium. After the reaction, the platinum-group metal catalyst can be filtered off together with the sparingly soluble activator, and be reused in further oxidation reactions. Losses of platinum-group metal catalyst and/or activator, if these occur, must be made up.

The activator may be added to the reactants as a solid, preferably in a finely divided form, or in the form of a solution. It is also possible to add the activator when preparing the platinum-group metal catalyst, or to impregnate the platinum-group metal catalyst with the activator. The activator can also serve as a support for the platinum metal.

The combination of platinum with lead and/or with bismuth has proved particularly suitable.

The process according to the invention is usually carried out by bring oxygen or a gas that contains molecular oxygen, such as air, into good contact with the solution of the arylethane-1,2-diol, containing the alkaline agent, the platinum-group metal catalyst and the activator. Usually, the reaction is carried out under atmospheric pressure (1 bar), but the oxidation can also be carried out under higher or lower pressures, for example in the range from 0.5 to 10 bar. The course of the reaction can be followed from the amount of oxygen taken up, and the reaction is discontined when the amount of oxygen theoretically required for the desired arylglyoxylic acid has been taken up. In most cases, the oxygen uptake automatically ceases, or slows down, at this stage. The progress of the reaction can also be followed by different means, for example by determining the arylglyoxylic acid formed.

For working up, the platinum-group metal catalyst together with undissolved activator is separated from the reaction mixture, for example by filtration. The arylglyoxylic acid is liberated from the alkaline reaction solution by acidification to a pH value below 6, and is separated off in accordance with known methods, such as decanting and/or filtration and/or extraction, and, if necessary is purified further, for example by recrystallisation, distillation or extraction.

The sequence in which platinum-group metal catalyst, activator, alkali and arylethane-1,2-diol are added is optional. Thus, the platinum-group metal catalyst and activator can be added to the aqueous alkaline arylethane-1,2-diol solution; it is also possible first to take the platinum-group metal catalyst and activator and to add aqueous alkaline arylethane-1,2-diol solution; finally, it is also possible to take the platinum-group metal catalyst, a part of the aqueous alkali and the activator, and to add the arylethane-1,2-diol together with the remaining alkali. Further, it is possible to add the activator to the mixture of the reactants.

The arylglyoxylic acids which can be prepared by the process according to the invention are valuable organic intermediates and of great importance, for example, for the preparation of plant protection agents, as well as of photocuring lacquers and of medicaments.

For example, the herbicidal active compound 3-methyl-4-amino-6-phenyl-1,2,4-triazin-5(4H)-one can be prepared starting from phenylglyoxylic acid (see DE-OS (German Published Specification) No. 2,224,161).

The preparative examples which follow illustrate the process according to the invention.

PREPARATIVE EXAMPLES

EXAMPLE 1

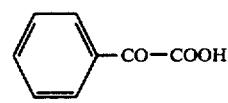
(1)

2 g of platinum-containing active charcoal (platinum content: 1% by weight), 1.5 ml of 0.1 molar $Pb(NO_3)_2$ solution (corresponding to an amount of lead of $1.5 \times 10^{-4}$ mole) and a solution of 13.8 g (0.1 mole) of ($\pm$)-phenylethylene-1,2-glycol in 100 ml of 1.3 N sodium hydroxide solution were introduced into a reaction vessel equipped with a stirrer, thermometer and gas inlet.

After displacing the air from the reaction vessel by means of oxygen, the stirrer was started and pure oxygen was introduced into the mixture under normal pressure at 70° C., with vigorous stirring. After 45 minutes, 0.15 mole of $O_2$ had been taken up and the oxygen uptake almost stopped.

After filtering off the catalyst, the content of phenylglyoxylic acid in the filtrate was determined by differential pulse polarography. The base electrolyte used was 1 N LiOH. The determination was carried out against a phenylglyoxylic acid solution of known strength, which was added as the internal standard when carrying out a repeat measurement. The determination showed a phenylglyoxylic acid yield of 93% of theory.

The phenylglyoxylic acid could also be liberated by acidification with sulphuric acid and—if necessary after filtering off the benzoic acid simultaneously produced in small amounts (0.6 g ≙ 5% of theory)—could be extracted from the solution, for example with ether, and be obtained, in the free form, after evaporation of the ether. The catalyst filtered off could be reused.

EXAMPLE 2

The procedure in Example 1 was followed, except that instead of lead, $3 \times 10^{-4}$ mole of bismuth in the form of its finely pulverulent nitrate $[Bi(NO_3)_3 \cdot 5H_2O]$ was added as the activator to the reaction mixture. After an oxidation time of 60 minutes, the stoichiometrically required amount of oxygen had been taken up and the polarographic determination showed a yield of phenylglyoxylic acid of 90% of theory. The catalyst could be reused after being filtered off.

EXAMPLES 3 TO 15

The procedure in Example 1 was followed, except that the reaction took place at 75° C. and with different activators and amounts of activators, as shown in Table 1:

TABLE 1

| Ex. No. | Activator Type | Mole of activator per mole of ($\pm$)-phenyl-ethylene-1,2-glycol | $O_2$ uptake Time in minutes | Amount in % of theory,[a] | Yield of phenyl-glyoxylic acid % of theory |
|---|---|---|---|---|---|
| 3[c] | without activator | | approx. 240 | 75[b] | 10 |

TABLE 1-continued

| Ex. No. | Activator Type | Mole of activator per mole of (±)-phenyl-ethylene-1,2-glycol | O₂ uptake Time in minutes | O₂ uptake Amount in % of theory,$^a$ | Yield of phenyl-glyoxylic acid % of theory |
|---|---|---|---|---|---|
| 4 | Pb(NO₃)₂ | $1 \times 10^{-5}$ | 90 | 87$^b$ | 37 |
| 5 | " | $5 \times 10^{-5}$ | 90 | 90$^b$ | 48 |
| 6 | " | $2,5 \times 10^{-4}$ | 60 | 98$^b$ | 76 |
| 7 | " | $5 \times 10^{-4}$ | 60 | 100 | 90 |
| 8 | " | $3 \times 10^{-3}$ | 40 | 100 | 93 |
| 9 | " | $6 \times 10^{-3}$ | 45 | 100 | 92 |
| 10 | Bi(NO₃)₃.5H₂O | $2 \times 10^{-5}$ | 120 | 86$^b$ | 48 |
| 11 | " | $2 \times 10^{-4}$ | 45 | 100 | 87 |
| 12 | " | $1 \times 10^{-3}$ | 50 | 100 | 87 |
| 13 | Pb-powder | $2 \times 10^{-3}$ | 75 | 100 | 90 |
| 14 | Pb₃O₄(red lead) | $4 \times 10^{-3}$ | 125 | 100 | 89 |
| 15 | (CH₃COO)₂Pb | $5 \times 10^{-4}$ | 60 | 100 | 90 |

$^a$100% of theory = 1.5 mols of O₂/mol of (±)-phenylethylene-1,2-glycol.
$^b$The reaction virtually stopped after this amount of O₂ had been taken up.
$^c$Comparative example.

As is shown in (Comparative) Example 3, the oxidation took place substantially more slowly if no activator was added. The oxygen uptake stopped prematurely and the yield of phenylglyoxylic acid was only 10% of theory.

EXAMPLE 16

The procedure in Example 1 was followed. A solution of 13.8 g (0.1 mole) of (±)-phenylethylene-1,2-glycol in 100 ml of 2 N sodium hydroxide solution was employed. 1.5 g of active charcoal (medicinal charcoal) containing 5% of palladium, and $2 \times 10^{-4}$ mole of Bi(NO₃)₃.5 H₂O were added to the solution. The oxidation was then carried out at 70° C. and 1 bar O₂ pressure. After 140 minutes, 0.15 mole of O₂ had been taken up and the yield of phenylglyoxylic acid was 45% of theory.

Without the addition of bismuth, the yield under otherwise identical conditions was only 10% of theory after 0.15 mole of O₂ had been taken up.

EXAMPLE 17

The procedure in Example 16 was followed, except that in place of bismuth, $1.5 \times 10^{-3}$ mole of lead (II) nitrate was added to the solution. In this case, the reaction time was 110 minutes and the yield of phenylglyoxylic acid was 40% of theory.

Without the addition of lead, the yield under otherwise identical conditions was only 10% of theory.

It will be understood that the specification and examples are illustrative but not limitative of the present invention and that other embodiments within the spirit and scope of the invention will suggest themselves to those skilled in the art.

What is claimed:

1. Process for the preparation of an arylglyoxylic acid of the formula $$Ar-CO-COOH$$

wherein Ar is optionally substituted aryl which process comprises oxidizing the corresponding arylethane-1,2-diol of the formula $$\underset{\underset{OH}{|}\phantom{xx}\underset{OH}{|}}{Ar-CH-CH_2} \tag{I}$$

wherein Ar is defined as above, with oxygen or a gas containing molecular oxygen in an aqueous alkaline medium, in the presence of a platinum-group metal catalyst and, as an activator, a material selected from lead, lead compounds, bismuth and bismuth compounds, at a temperature of up to the boiling point of the reaction mixture.

2. Process as claimed in claim 1 wherein Ar is phenyl.

3. Process as claimed in claim 1 wherein Ar is naphthyl.

4. Process as claimed in claim 1 wherein said activator material is present in an amount of from $5 \times 10^{-5}$ to $1 \times 10^{-1}$ mole per mole of arylethane-1,2-diol.

5. Process as claimed in claim 1 wherein said activator material is present in an amount of from $1 \times 10^{-4}$ to $1 \times 10^{-2}$ mole per mole or arylethane-1,2-diol.

6. Process as claimed in claim 1 wherein said activator material is lead in elemental form.

7. Process as claimed in claim 1 wherein said activator material is bismuth in elemental form.

8. Process as claimed in claim 1 wherein said activator material is lead in oxide or hydracid salt form.

9. Process as claimed in claim 1 wherein said activator material is bismuth in oxide or hydracid salt form.

10. Process as claimed in claim 1 wherein said activator material is lead in the form of a salt of an inorganic oxyacid, a transition-metal-containing oxyacid or an organic aliphatic or aromatic acid.

11. Process as claimed in claim 1 wherein said activator material is bismuth in the form of a salt of an inorganic oxyacid, a transition-metal-containing oxyacid or an organic aliphatic or aromatic acid.

12. Process as claimed in claim 1 wherein platinum is the platinum-group metal catalyst.

13. Process as claimed in claim 1 wherein palladium is the platinum-group metal catalyst.

14. Process as claimed in claim 1 wherein said activator material is one of lead and bismuth and is incorporated into the platinum-group metal catalyst.

15. Process as claimed in claim 1 wherein said platinum-group metal catalyst is a supported catalyst.

16. Process as claimed in claim 15 wherein an active charcoal is used as the support.

17. Process as claimed in claim 15 wherein the platinum-group metal content of the supported catalyst is less than 10% by weight.

18. Process as claimed in claim 17 wherein the platinum-group metal content of the supported catalyst is 0.1 to 5% by weight.

19. Process as claimed in claim 1 wherein said platinum-group metal is employed in amount less than 1000 mg per mole of arylethane-1,2-diol.

20. Process as claimed in claim 19 wherein said platinum-group metal is employed in amount 20 to 400 mg per mole of arylethane-1,2-diol.

21. Process as claimed in claim 1 wherein said alkali is sodium hydroxide or potassium hydroxide.

22. Process as claimed in claim 1 wherein said alkali is employed in an amount of 0.3 to 5 equivalents per mole of arylethane-1,2-diol.

23. Process as claimed in claim 1 wherein said alkali is employed in an amount of 0.5 to 3 equivalents per mole of arylethane-1,2-diol.

24. Process as claimed in claim 1 wherein said alkali is employed in an amount of 0.9 to 2 equivalents per mole of arylethane-1,2-diol.

25. Process as claimed in claim 1 wherein the process is carried out at a temperature of from 10° to 100° C.

26. Process as claimed in claim 1 wherein the process is carried out with oxygen or an oxygen-containing gas under a pressure of 0.5–10 atmospheres.

27. Process as claimed in claim 1 wherein Ar is substituted phenyl wherein the substituents are selected from alkyl, cycloalkyl, aryl, aralyl, alkoxy, cycloalkoxy, aryloxy, hydroxyl, carboxyl, halogen and methylenedioxy.

28. Process as claimed in claim 1 wherein said arylethane-1,2-diol of formula I is phenylethylene-1,2-glycol.

29. Process as claimed in claim 1, for making phenylglyoxylic acid which process comprises reacting phenylethane-1,2-glycol with platinum-containing active charcoal and lead or a lead compound as an activator material, in a sodium hydroxide solution at a temperature of from 1° to 100° C.

30. Process as claimed in claim 1, for making phenylglyoxylic acid which process comprises reacting phenylethane-1,2-glycol with platinum-containing active charcoal and bismuth or a bismuth compound as an activator material, in a sodium hydroxide solution at a temperature of from 1° to 100° C.

* * * * *